United States Patent
Marhsall et al.

(10) Patent No.: US 8,096,420 B2
(45) Date of Patent: Jan. 17, 2012

(54) UNIVERSAL BLISTER PACKAGE

(75) Inventors: Paul T. Marhsall, Cincinnati, OH (US); Mark S. Leuenberger, Loveland, OH (US); Robert A. Allison, Loveland, OH (US); Paul W. Boentges, West Chester, OH (US); Jeffrey A. Brewer, Wyoming, OH (US); Joseph C. Hueil, Loveland, OH (US); Kevin R. O'Brien, Cincinnati, OH (US); Jerold J. Sanchez, Albuquerque, NM (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 12/112,049

(22) Filed: Apr. 30, 2008

(65) Prior Publication Data
US 2009/0272664 A1 Nov. 5, 2009

(51) Int. Cl.
*B65D 81/05* (2006.01)
*B65D 81/07* (2006.01)
(52) U.S. Cl. .................... 206/583; 206/363
(58) Field of Classification Search ............ 206/583, 206/806, 521, 592, 778, 363, 461, 497, 305, 206/438, 779, 565
See application file for complete search history.

(56) References Cited

U.S. PATENT DOCUMENTS

| 4,491,225 | A | * | 1/1985 | Baillod | 206/583 |
|---|---|---|---|---|---|
| 4,852,743 | A | * | 8/1989 | Ridgeway | 206/583 |
| 4,903,827 | A | * | 2/1990 | Phelps et al. | 206/204 |
| 5,183,159 | A | | 2/1993 | Hojnacki | |
| 5,388,701 | A | * | 2/1995 | Ridgeway | 206/583 |
| 5,769,235 | A | * | 6/1998 | Keach et al. | 206/583 |
| 6,889,839 | B1 | | 5/2005 | Rosten | |
| 2002/0192107 | A1 | | 12/2002 | Hickey | |
| 2006/0102509 | A1 | * | 5/2006 | Powers et al. | 206/497 |
| 2007/0284281 | A1 | * | 12/2007 | Shimazu et al. | 206/592 |

FOREIGN PATENT DOCUMENTS

| EP | 0557804 | 9/1993 |
|---|---|---|
| EP | 0968932 | 1/2000 |
| WO | WO84/03483 | 9/1984 |

* cited by examiner

*Primary Examiner* — Steven A. Reynolds
(74) *Attorney, Agent, or Firm* — Welsh Flaxman & Gitler LLC (57) ABSTRACT

A universal blister package for the distribution of medical instruments includes a tray having a resilient film and a retainer having a resilient film. The tray and the retainer are shaped and dimensioned for selective engagement in a manner creating a storage space between the film of the tray and the film of the retainer for accommodating a medical instrument between the tray and the retainer.

5 Claims, 7 Drawing Sheets

UNIVERSAL BLISTER PACKAGE

BACKGROUND OF THE INVENTION

1. Field of the Invention

The invention relates to packaging. More particular, the invention relates to universal packaging for medical instruments.

2. Description of the Related Art

As those familiar with the medical instrument industry will certainly appreciate, products must be shipped and packaged in a manner that maintains their sterility and protects the instruments during shipping. As such, most medical instrument packaging is constructed in a manner specific to the instrument at issue. As such, substantial tooling and costs are applied in developing individual unique packaging for each medical instrument.

With the foregoing in mind, there is a need for packaging offering a mechanism whereby the costs and time expenditures associated with prior packaging techniques are obviated. The present invention provides such packaging.

SUMMARY OF THE INVENTION

It is, therefore, an object of the present invention to provide a universal blister package for the distribution of medical instruments. The blister package includes a tray having a resilient film and a retainer having a resilient film. The tray and the retainer are shaped and dimensioned for selective engagement in a manner creating a storage space between the film of the tray and the film of the retainer for accommodating a medical instrument between the tray and the retainer.

It is also an object of the present invention to provide a blister package wherein the tray includes a tray body having a base from which a plurality of upwardly extending sidewalls depend. The base includes a perimeter edge and the upwardly extending sidewalls are positioned along the perimeter edge of the base. The retainer includes a retainer body having an open base from which a plurality of downwardly extending sidewalls depend. The base includes a perimeter edge and the downwardly extending sidewalls are positioned along the perimeter edge of the base.

It is another object of the present invention to provide a blister package wherein the base and upwardly extending sidewalls of the tray body define an exterior surface of the tray body that is substantially convex, the base and upwardly extending sidewalls of the retainer body define an interior surface of the retainer body in the shape of a recess in which a medical product is supported, the base and downwardly extending sidewalls of the tray body define an exterior surface of the tray body, and the base and downwardly extending sidewalls of the retainer body define an interior surface of the retainer body in the shape of a recess in which a medical instrument is retained.

It is a further object of the present invention to provide a blister package wherein the film of the tray is applied along the interior surface of the tray body and the film of the retainer is applied along the interior surface of the retainer body.

It is also an object of the present invention to provide a blister package wherein the film includes a first surface facing away from the base of the tray body and a second surface facing the base of the tray body, and the film includes a first surface facing away from the base of the retainer body and a second surface facing the base of the retainer body.

It is another object of the present invention to provide a blister package wherein the film is adhered to a ledge located on the interior surface of the upwardly extending sidewalls making up the tray body, wherein the medical instrument is packaged such that it is placed upon the first surface of the film with the film between the base of the tray body and the medical instrument, as well as supporting and spacing the medical instrument away from the base of the tray body, and wherein the film is adhered to a ledge located on the interior surface of the upwardly extending sidewalls making up the retainer body, wherein the medical instrument is packaged such that it is placed upon the first surface of the film with the film between the base of the retainer body and the medical instrument, as well as supporting and spacing the medical instrument away from the base of the retainer body.

It is a further object of the present invention to provide a blister package wherein upper edges of the upwardly extending sidewalls of the tray body are provided with coupling members shaped and dimensioned to receive mating coupling members at the edges of the downwardly extending sidewalls of the retainer body.

It is also an object of the present invention to provide a blister package wherein the assembled blister package is then wrapped and sealed in a sheet.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 6, a universal blister package 10 is disclosed. The present blister package 10 is particularly designed for use in the distribution of medical instruments 12, although those skilled in the art will appreciate the concepts underlying the present blister package 10 may be applied to the distribution of various products without departing from the spirit of the present invention. The present blister package 10 eliminates the need for the design and manufacture of a custom blister package for each new product developed and also eliminates the need for many, if not most, of the blister packages currently being used in production.

In accordance with a preferred embodiment, the present blister package 10 includes a tray 14 and a retainer 16. As will be discussed below in greater detail, the tray 14 and retainer 16 are shaped and dimensioned for selective engagement in a manner creating a storage space 18 accommodating a medical instrument(s) 12 between the tray 14 and the retainer 16.

The tray 14 includes a tray body 20. The tray body 20 is preferably composed of thermoformed PETG (polyethylene terephthalate glycol). The tray body 20 is generic and may support a variety of medical instruments. The tray body 20 is, therefore, constructed with a base 22 from which a plurality of upwardly extending sidewalls 24 extend. The base 22 includes a perimeter edge 26 and the upwardly extending sidewalls 24 are positioned along the perimeter edge 26 of the base 22.

The base 22 and upwardly extending sidewalls 24 define an exterior surface 28 that is substantially convex. The base 22 and upwardly extending sidewalls 24 define an interior surface 30 in the shape of a recess 32 in which a medical product is supported in a manner discussed below in greater detail.

The tray 14 further includes a thin resilient film 34. In accordance with a preferred embodiment of the present invention, the thin resilient film is a medical grade polyurethane material, although is contemplated other resilient film materials could be employed within the spirit of the present invention. For example, it is contemplated the film could be a polypropylene or polyethylene type material providing that the material properties meet the performance requirements that enable functionality of the present package.

The film 34 is applied along the interior surface 30 of the tray body 20. In particular, the film 34 includes a first surface 36 facing away from the base 22 of the tray body 20 and a second surface 38 facing the base 22 of the tray body 20. The film 34 is adhered to a ledge 40 located on the interior surface 30 of the upwardly extending sidewalls 24 making up the tray body 20. In practice, the medical instrument(s) 12 is packaged such that it is placed upon the first surface 36 of the film 34 with the film 34 between the base 22 of the tray body 20 and the medical instrument(s) 12, as well as supporting and spacing the product away from the base 22 of the tray body 20.

The blister package 10 further includes a retainer 16. The retainer 16 is constructed much like the tray 14 and includes a retainer body 42. As such, the retainer body 42 is constructed with an open base (or structural support rim) 44 from which a plurality of downwardly extending sidewalls 46 depend. The base 44 includes a perimeter edge 48 and the downwardly extending sidewalls 46 are positioned along the perimeter edge 48. The base 44 and downwardly extending sidewalls 46 define an exterior surface 50. The base 44 and downwardly extending sidewalls 46 define an interior surface 52 in the shape of a recess 54 in which a medical instrument(s) 12 is retained in a manner discussed below in greater detail.

As with the tray 14, the retainer 16 also includes a thin resilient film 56 adhered to a ledge 58 within the retainer body 42. In particular, the film 56 is applied along the interior surface 52 of the retainer body 42. The film 56 includes a first surface 60 facing away from the base 44 of the retainer body 42 and a second surface 62 facing the base 44 of the retainer body 42. The film 56 is adhered to the ledge 58 located on the interior surface 52 of the downwardly extending sidewalls 46 making up the retainer body 42. As will be discussed below in greater detail, the medical instrument(s) 12 is packaged such that it is placed on the first surface 60 of the film 56 with the film 56 between the base 44 of the retainer 16 and the medical instrument(s) 12. As with the tray 14, the film 56 supports and retains the medical instrument(s) 12 in a spaced relationship relative to the base 44 of the retainer body 42.

In practice, the medical instrument(s) 12 is placed within the tray 14 and upon the first surface 36 of film 34 mounted therein. As shown in the appended drawings, during packaging of a medical instrument(s) 12 the tray 14 is preferably supported in a horizontal orientation with the recess 32 and film 34 facing upwardly and ready to receive the medical instrument(s) 12. Although this orientation is preferred and used in describing the operation of the present blister package 10, it is contemplated other orientations are possible without departing from the spirit of the present invention. Once the medical instrument(s) 12 is placed in the recess 32 defined by the tray 14 and upon the first surface 36 of the film 34, the retainer 16 is positioned above the tray 14 and the downwardly extending sidewalls 46 of the retainer body 42 are engaged with the upwardly extending sidewalls 24 of the tray body 20 to form a cavity, or storage space 18, in which the medical instrument(s) 12 is positioned.

In accordance with a preferred embodiment, the upper edges 64 of the upwardly extending sidewalls 24 of the tray body 20 are provided with coupling members 66 shaped and dimensioned to receive mating coupling 68 members at the edges 70 of the downwardly extending sidewalls 46 of the retainer body 42. The coupling members 68 of the respective tray body 20 and retainer body 42 preferable snap into engagement to hold the retainer 16 relative to the tray 14. By snapping the retainer 16 in place over the tray 14, and as a result of the mechanical nature of the films 34, 56, the medical instrument(s) 12 is suspended within the blister package 10; that is, the medical instrument(s) 12 is supported generally between the tray body 20 and the retainer body 42 with the respective films 34, 56 of the tray 14 and retainer 16 holding the medical instrument(s) 12 in a spaced relationship from the respective bases 22, 44 of the tray body 20 and retainer body 42.

Figure 1:
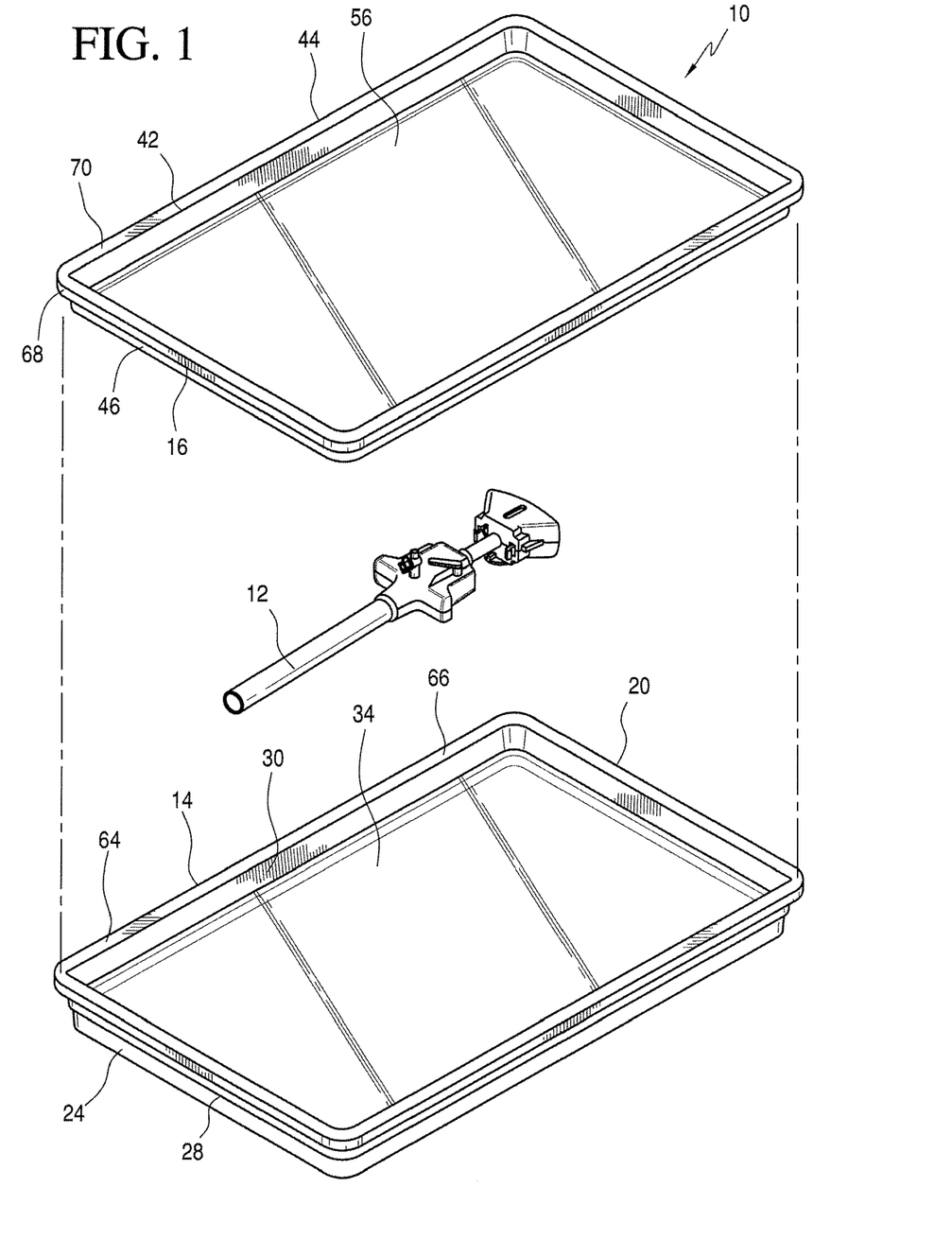
FIG. 1 is an exploded perspective view of a package in accordance with a first embodiment of the present invention.
Figure 2:
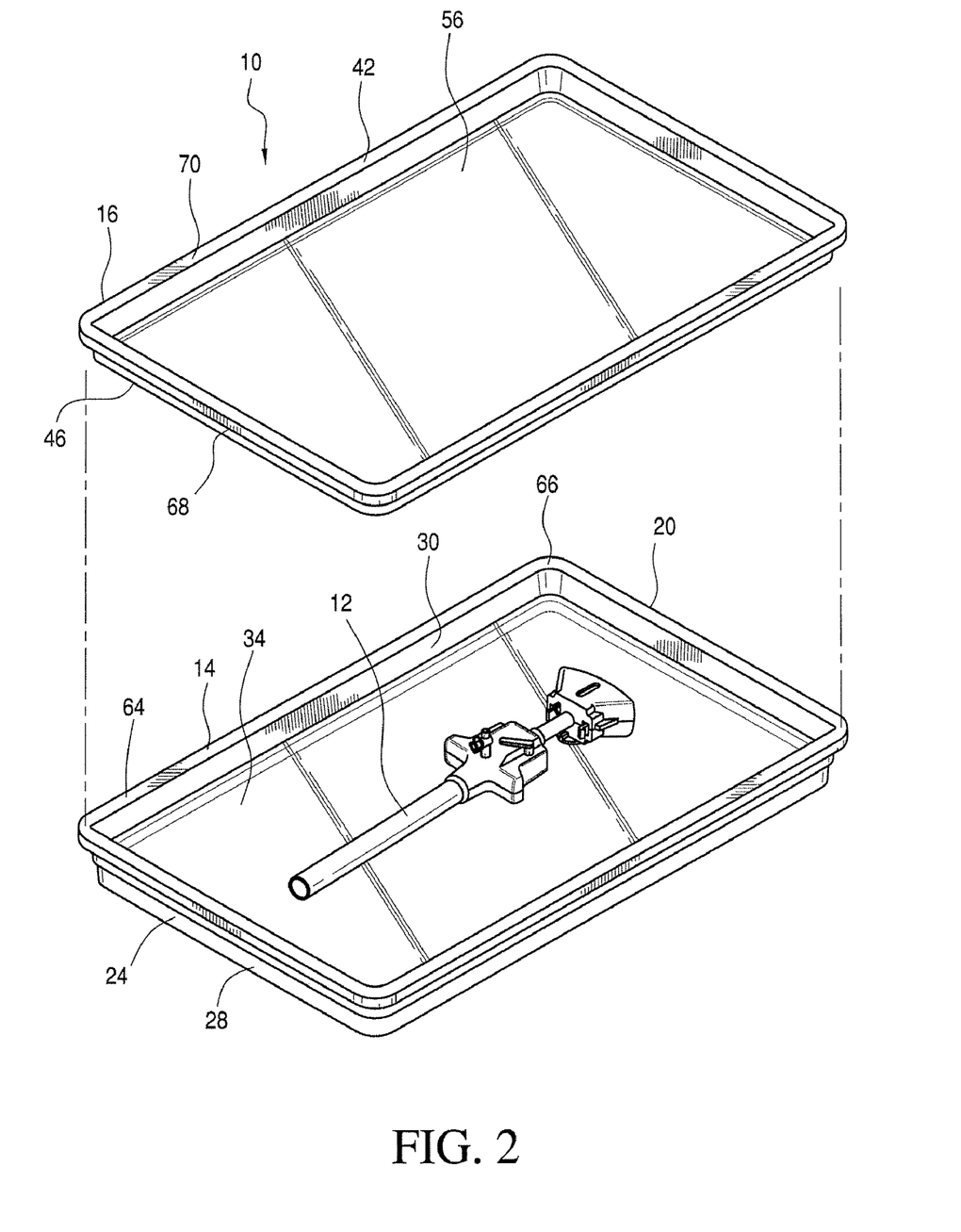
FIG. 2 is an exploded perspective view of the package shown with reference to FIG. 1 with a medical instrument ready for packaging.
Figure 3:
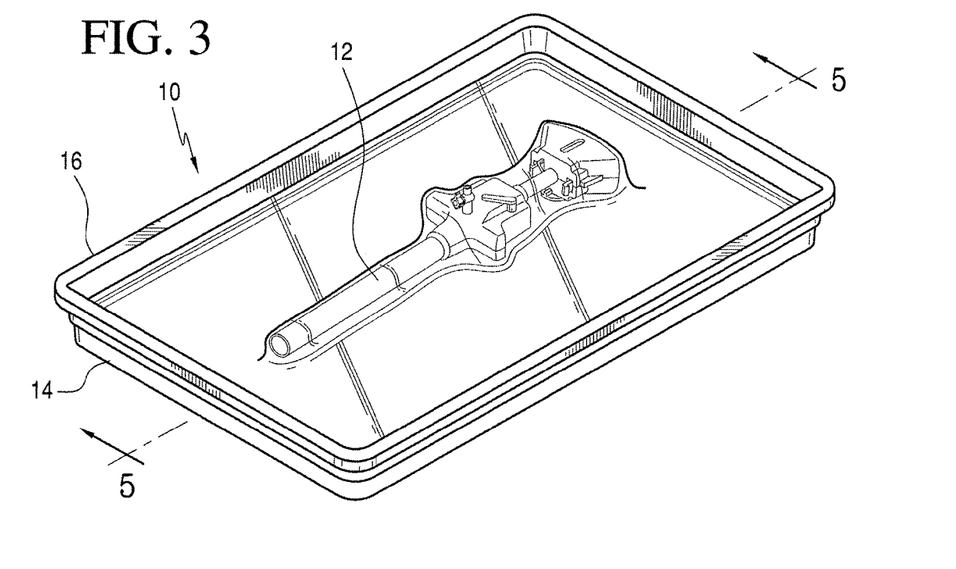
FIGS. 3 and 4 show perspective views of the medical instrument sealed within the package.
Figure 4:
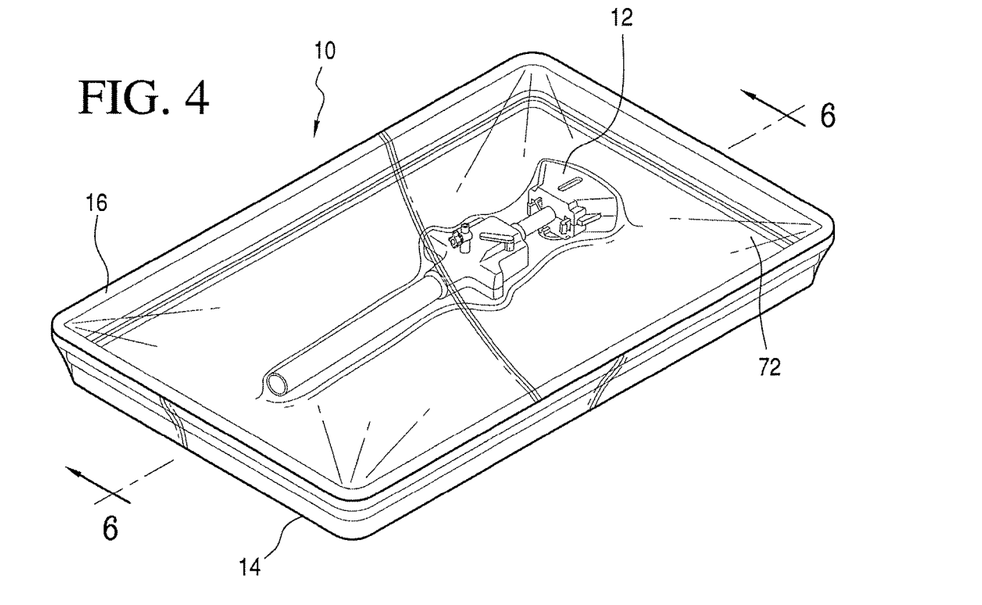
Figure 5:
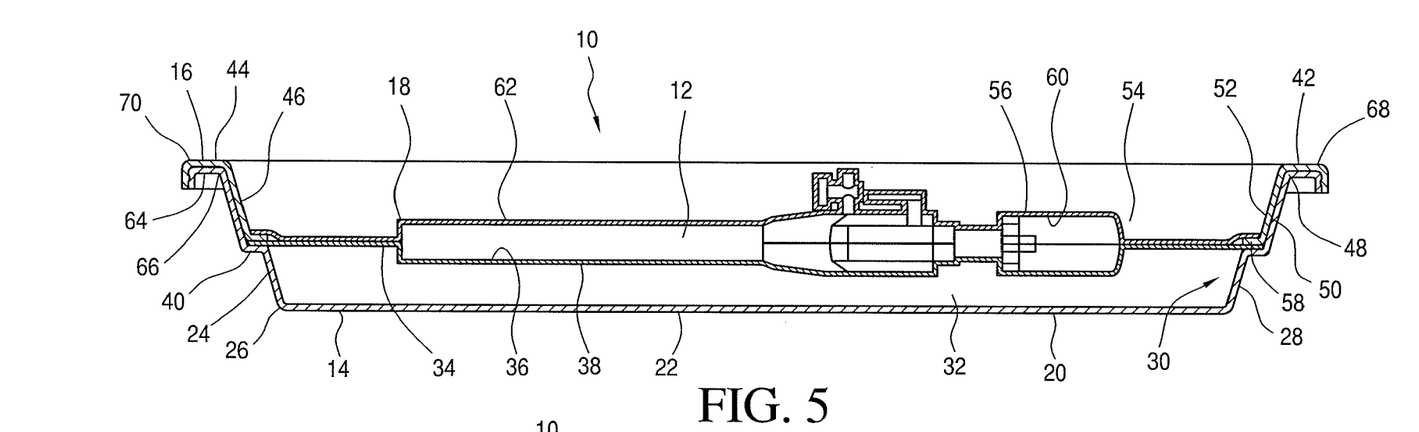
FIGS. 5 and 6 show cross sectional views of the medical instrument of FIGS. 3 and 4, respectively sealed within the package with TYVEK wrapping the package.
Figure 6:
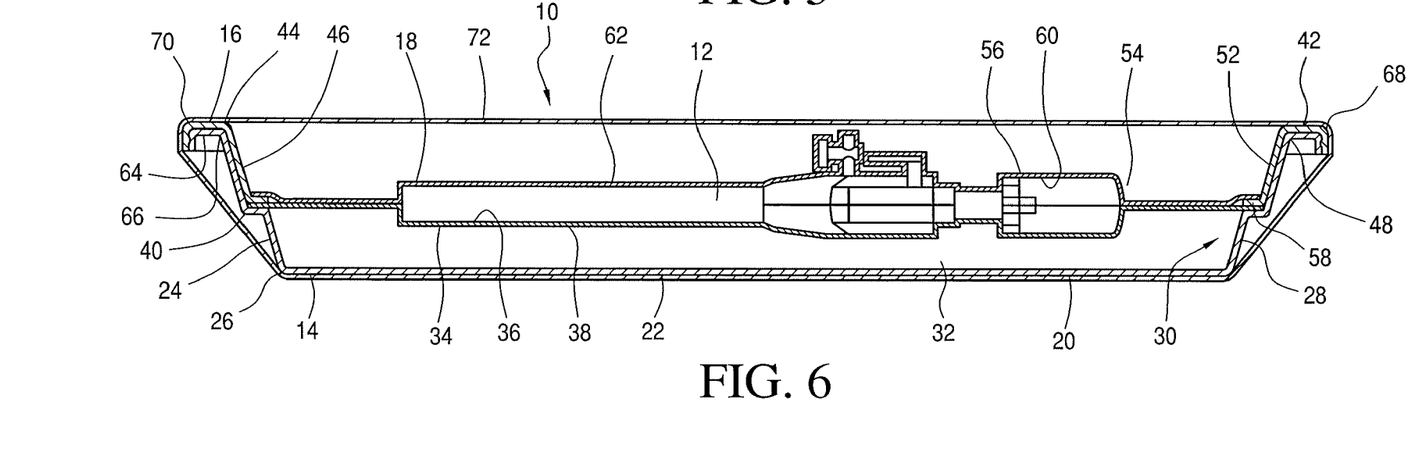

The assembled blister package 10 is then wrapped and sealed with TYVEK® (a sheet of man-made fibers, for example, a spunbonded olefin) 72 in a conventional manner in order to ensure sterility. While TYVEK is disclosed in accordance with a preferred embodiment, it is contemplated other suitable medical grade lidding materials may be used without departing from the spirit of the present invention. As those skilled in the art will certainly appreciate, it is contemplated the present blister package 10 will be constructed in various sizes to accommodate several product families.

In accordance with an alternate embodiment, and with reference to FIGS. 7 to 12, a package 110 is disclosed which includes an inner tray 114 with a vacuum sealed pouch 116 secured thereabout in a manner securely holding a medical instrument(s) 112 between the inner tray 114 and the pouch 116. More particularly, the package 110 includes a rigid or semi-rigid inner tray 114. The inner tray 114 is preferably manufactured from paperboard, foam or plastic, although other materials may be used without departing from the spirit of the present invention. The inner tray 114 includes a base 118 with raised sidewalls 120 extending therefrom. The base 118 includes a perimeter edge 122 and the sidewalls 120 are positioned along the perimeter edge 122. In accordance with a preferred embodiment, the inner tray 114 is sized such that a medical instrument 112, or a set of medical instruments, may be laid out along the base 118 of the inner tray 114 while still providing clearance between the instrument(s) and between the instrument(s) and the sidewalls 120 of the inner tray 114.

Figure 9:
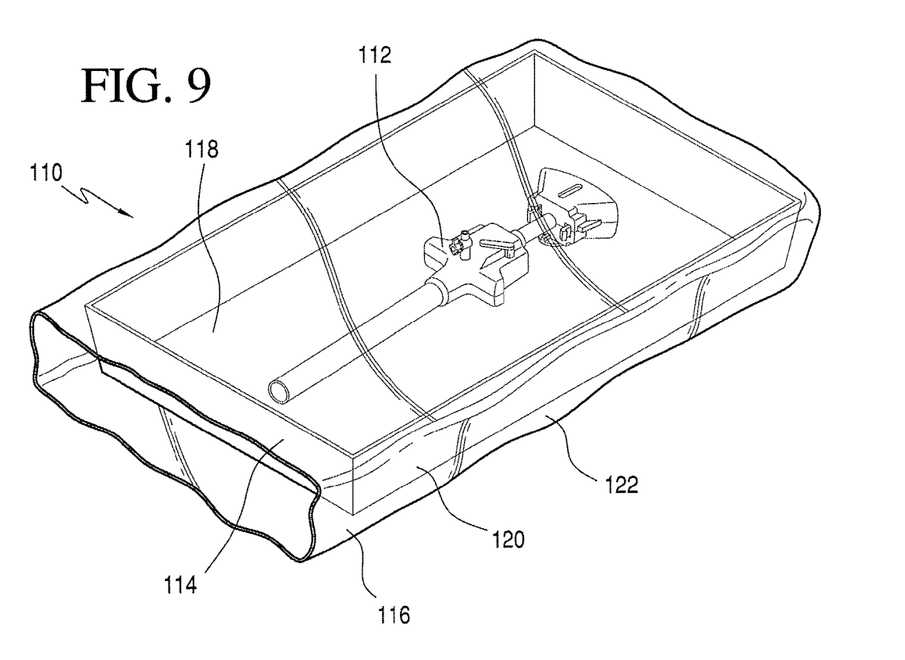
FIG. 9 is a perspective view of the medical instrument ready for packaging with a pouch positioned about the tray.
Figure 10:
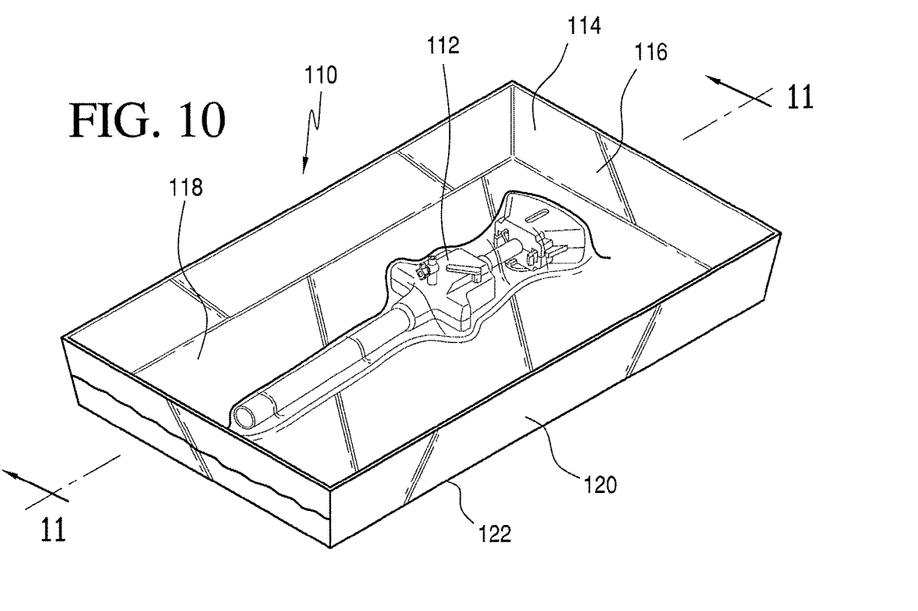
FIGS. 10 and 11 respectively show a perspective view and a cross sectional view of the medical instrument sealed in accordance with the present invention.
Figure 11:
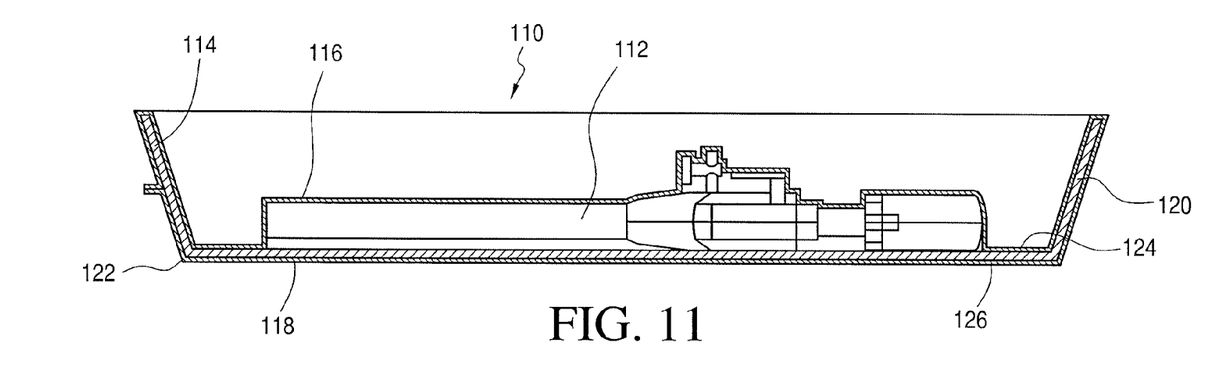

The package 110 further includes a nonporous plastic film bag or pouch 116 shaped and dimensioned to fit over the inner tray 114 with the medical instrument(s) 112 positioned thereon. As will be discussed below in greater detail, the pouch 116 is constructed to permit the formation of a sealed vacuum environment within the pouch 116.

As such, and in practice, the inner tray 114, with the medical instrument(s) 112 in its designated position, is positioned within the pouch 116. The air within the pouch 116 is drawn from the pouch 116 via a vacuum, evacuating the space within the pouch 116. The pouch 116 is then immediately vacuum sealed with all air removed from the interior of the pouch 116.

Figure 12:
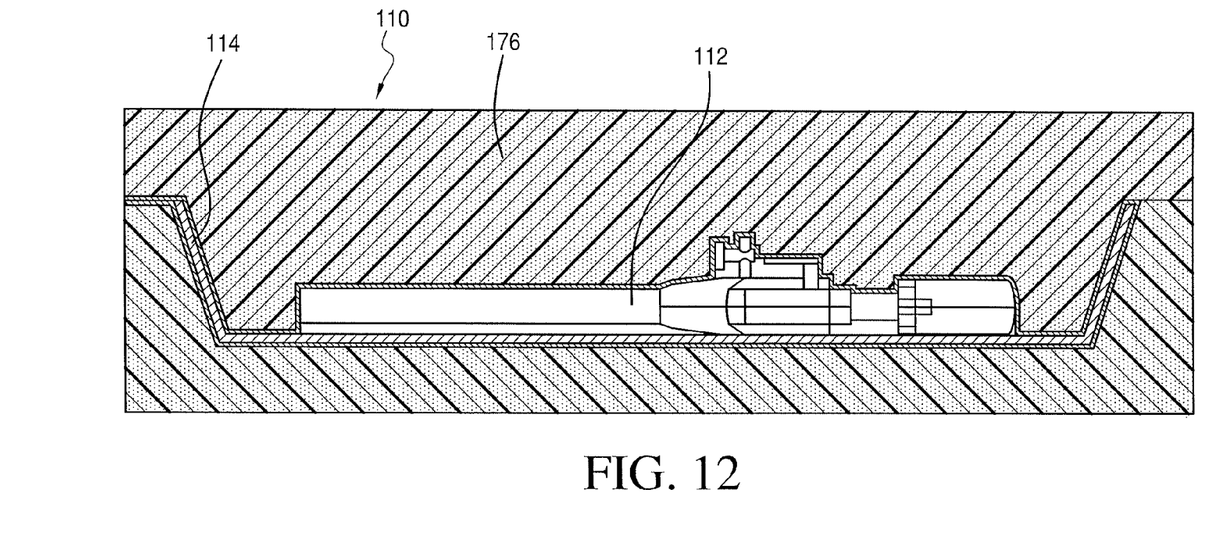
FIG. 12 is a cross sectional view showing foam positioned about the sealed package.

Although it is contemplated evacuation and sealing of the pouch 116 is to be achieved through the implementation of an automated process, it is further contemplated evacuation and sealing may be achieved through manual compression of the pouch and inner tray 114 with soft foam 176 during sealing, thus pushing the air out of the pouch 116 (see FIG. 12).

With the medical instrument(s) 112 sealed within the pouch 116 as described above, the film of the pouch 116 is drawn into engagement with the inner tray 114 along the exposed top and bottom surfaces 124, 126 of the inner tray 114 and directly around the medical instrument(s) 112 precluding movement of the medical instrument(s) 112 relative to the inner tray 114 and thereby retaining the medical instrument 112 against the base of the inner tray 114. As such, the present package 110 is composed of an inner tray 114 with a vacuum sealed pouch 116 secured thereabout in a manner securely holding a medical instrument 112 between the inner tray 114 and the pouch 116. The present package 110 precludes the movement of the device features, such as, for example, handles, triggers, etc.

The present invention allows faster product launches due to its ability to provide a more generic universal packaging component, thus eliminating the need for custom formed tooling in the production of a package. The present invention also provides a benefit for products with anticipated design changes that normally would require package tooling revisions and revalidations to implement design changes.

Figure 7:
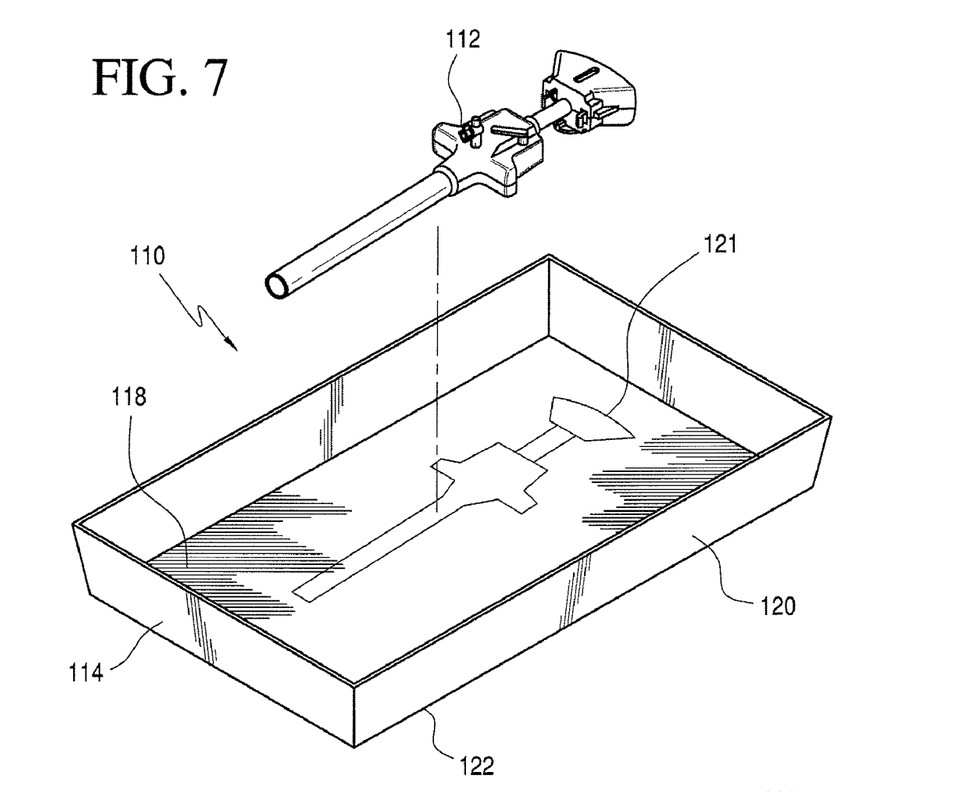
FIG. 7 is an exploded perspective view of a medical instrument being placed into a tray of a package in accordance with a second embodiment of the present invention.
Figure 8:
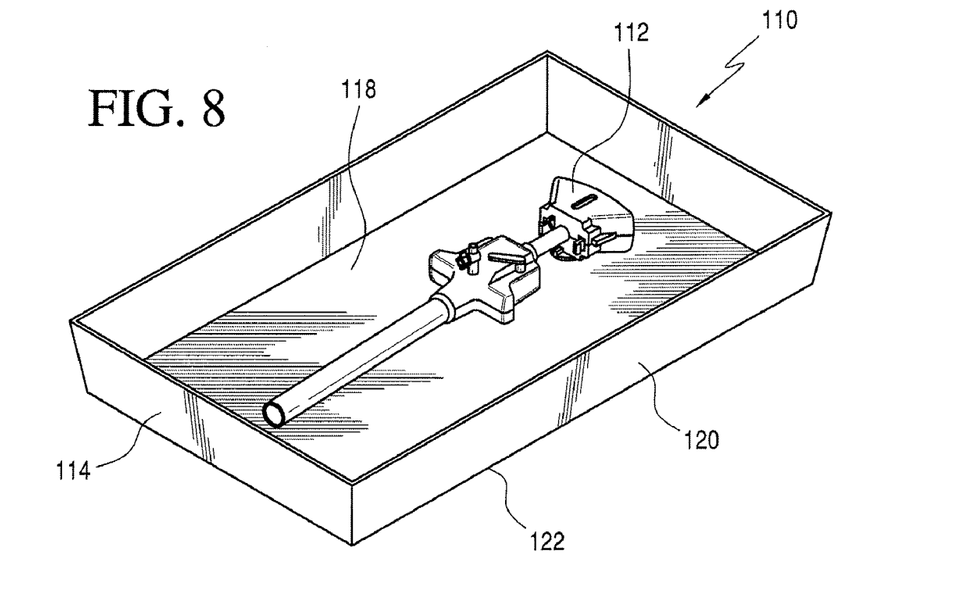
FIG. 8 is a perspective view of the tray shown with reference to FIG. 7 with a medical instrument ready for packaging.

Possible additional features of the present invention includes the ability of a manufacturer to print device outlines 121 in the bottom or other exposed surfaces of the inner tray or on separate paper inserts into the inner tray that show the planned positioning of the medical instruments into the inner tray and/or require product labeling printed on the bottom of the inner tray or on a separate sheet inserted into the bag such that the printed pouches would not be required. In addition, it is contemplated the inner tray could either be made of foam or have a foam layer inserted into the bottom of the inner tray to provide cushioning to the product.

The present invention also allows for irregular or sharp features of a medical product to be provided with a separate protective cover of foam or paperboard or plastic such that when the air is removed from the pouch, the cover remains between the pouch material and the medical product to prevent abrasion or holes in the pouch from the product.

It is further contemplated that the present invention will provide a ready indication of breach of sterility in that a hole in the pouch will inherently result in a loose fitting pouch due to the ingress of additional air into the interior of it versus otherwise sealed package product without holes in the pouch.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A universal blister package for distribution of medical instruments, consisting essentially of:
a tray including a resilient tray film, the tray includes a tray body including a base from which a plurality of upwardly extending sidewalls depend, the base includes a perimeter edge and the upwardly extending sidewalls are positioned along the perimeter edge of the base, the upwardly extending sidewalls including upper edges, wherein the base and upwardly extending sidewalls of the tray body define an exterior surface of the tray body that is substantially convex and the base and upwardly extending sidewalls of the tray body define an interior surface of the tray body, the interior surface of the tray body being provided with a ledge to which the resilient tray film is adhered; and
a retainer including a resilient retainer film, the retainer includes a retainer body including an open base from which a plurality of downwardly extending sidewalls depend, the base includes a perimeter edge and the downwardly extending sidewalls are positioned along the perimeter edge of the base, the downwardly extending sidewalls including edges, wherein the base and downwardly extending sidewalls of the retainer body define an interior surface of the retainer body in the shape of a recess in which a medical instrument is supported and the base and downwardly extending sidewalls define an exterior surface, the interior surface of the retainer body being provided with a ledge to which the resilient retainer film is adhered;
wherein the tray and the retainer are shaped and dimensioned for selective engagement in a manner creating a storage space between the tray film and the retainer film for accommodating a medical instrument between the tray and the retainer, and wherein the downwardly extending sidewalls of the retainer body are shaped and dimensioned for engagement with the upwardly extending sidewalls of the tray body upon engagement of the tray and retainer,
wherein the medical instrument is placed within the tray and upon the tray film and the retainer is positioned above the tray and the downwardly extending sidewalls of the retainer body are engaged with the upwardly extending sidewalls of the tray body to form a storage space in which the medical instrument is positioned between the tray film and the retainer film.

2. The blister package according to claim 1, wherein the tray film includes a first surface facing away from the base of the tray body and a second surface facing the base of the tray body, and the retainer film includes a first surface facing away from the base of the retainer body and a second surface facing the base of the retainer body.

3. The blister package according to claim 2, wherein the medical instrument is packaged such that it is placed upon the first surface of the tray film with the tray film between the base of the tray body and the medical instrument, as well as supporting and spacing the medical instrument away from the base of the tray body, and wherein the medical instrument is packaged such that it is placed upon the first surface of the retainer film with the retainer film between the base of the retainer body and the medical instrument, as well as supporting and spacing the medical instrument away from the base of the retainer body.

4. The blister package according to claim 3, wherein the upper edges of the upwardly extending sidewalls of the tray body are provided with coupling members shaped and dimensioned to receive mating coupling members at the edges of the downwardly extending sidewalls of the retainer body.

5. The blister package according to claim 4, wherein the assembled blister package is then wrapped and sealed in a sheet.

* * * * *